United States Patent
Chen et al.

(10) Patent No.: US 10,136,888 B2
(45) Date of Patent: Nov. 27, 2018

(54) CIRCULAR STAPLER AND STAPLE HEAD ASSEMBLY THEREOF

(71) Applicant: Touchstone International Medical Science Co., Ltd., Jiangsu (CN)

(72) Inventors: Wangdong Chen, Jiangsu (CN); Teng Shan, Jiangsu (CN)

(73) Assignee: TOUCHSTONE INTERNATIONAL MEDICAL SCIENCE CO., LTD., Jiangsu (CN)

( * ) Notice: Subject to any disclaimer, the term of this patent is extended or adjusted under 35 U.S.C. 154(b) by 457 days.

(21) Appl. No.: 14/750,848

(22) Filed: Jun. 25, 2015

(65) Prior Publication Data
US 2015/0289872 A1    Oct. 15, 2015

Related U.S. Application Data

(63) Continuation of application No. PCT/CN2013/090449, filed on Dec. 25, 2013.

(30) Foreign Application Priority Data

Dec. 26, 2012  (CN) .......................... 2012 1 0573705

(51) Int. Cl.
 A61B 17/068   (2006.01)
 A61B 17/115   (2006.01)
 A61B 17/072   (2006.01)

(52) U.S. Cl.
 CPC ........ *A61B 17/068* (2013.01); *A61B 17/1155* (2013.01); *A61B 2017/07257* (2013.01); *A61B 2017/07285* (2013.01)

(58) Field of Classification Search
 CPC .............. A61B 17/1155; A61B 17/068; A61B 2017/07257; A61B 2017/00862;
 (Continued)

(56) References Cited

U.S. PATENT DOCUMENTS 5,397,324 A *  3/1995  Carroll ............. A61B 17/07207
                                              128/898
5,588,579 A * 12/1996  Schnut ................ A61B 17/115
                                              227/175.1
(Continued)

FOREIGN PATENT DOCUMENTS

CN    1915180 A    2/2007
CN  103156660 A    6/2013
CN  203029303 U    7/2013

OTHER PUBLICATIONS

International Search Report, dated Apr. 3, 2014, for International Application No. PCT/CN2013/090449, 8 pages.

*Primary Examiner* — Robert Long
(74) *Attorney, Agent, or Firm* — Seed IP Law Group

(57) ABSTRACT

A circular stapler includes a staple body and an anvil assembly. The staple body includes an annular staple cartridge and an annular cutter located at a distal end thereof. The anvil assembly includes an annular anvil, an annular cutting pad and an anvil shaft. When the staple body and the anvil assembly are closed, the annular staple cartridge is associated with the annular anvil and the annular cutting pad to form at least two connected fixing spaces having height difference. The circular stapler facilitates fixing the severed staples for easily cutting. A buffer may be formed between the tissues near the new formed staples and the tissue near the severed staples in order to avoid or reduce lateral slipping, thereby reducing dragging the tissues on the end face of the anvil.

18 Claims, 8 Drawing Sheets

(58) Field of Classification Search
CPC ...... A61B 2017/292; A61B 2017/2931; A61B 2017/07285
USPC ............ 227/175.1–182.1; 606/216, 219–221
See application file for complete search history.

(56) References Cited

U.S. PATENT DOCUMENTS

| | | | | |
|---|---|---|---|---|
| 6,325,810 | B1* | 12/2001 | Hamilton | A61B 17/07207 227/175.1 |
| 8,393,516 | B2* | 3/2013 | Kostrzewski | A61B 17/072 227/179.1 |
| 9,055,941 | B2* | 6/2015 | Schmid | A61B 17/00491 |
| 2005/0187576 | A1* | 8/2005 | Whitman | A61B 17/115 606/219 |
| 2005/0228414 | A1 | 10/2005 | Mayoral | |
| 2007/0034666 | A1 | 2/2007 | Holsten et al. | |
| 2007/0034668 | A1* | 2/2007 | Holsten | A61B 17/068 227/179.1 |
| 2009/0206139 | A1* | 8/2009 | Hall | A61B 17/07207 227/176.1 |
| 2010/0327042 | A1* | 12/2010 | Amid | A61B 17/0684 227/176.1 |
| 2011/0049213 | A1* | 3/2011 | Schneider | B25C 5/025 227/120 |
| 2012/0080334 | A1* | 4/2012 | Shelton, IV | A61B 90/92 206/339 |
| 2012/0175401 | A1* | 7/2012 | Bachman | A61B 17/0684 227/177.1 |
| 2012/0273547 | A1* | 11/2012 | Hodgkinson | A61B 17/07207 227/176.1 |
| 2013/0075450 | A1* | 3/2013 | Schmid | A61B 17/00491 227/178.1 |
| 2013/0153639 | A1* | 6/2013 | Hodgkinson | A61B 17/1114 227/180.1 |
| 2013/0256366 | A1* | 10/2013 | Shelton, IV | A61B 17/07207 227/175.1 |
| 2014/0197224 | A1* | 7/2014 | Penna | A61B 17/1155 227/179.1 |
| 2017/0027569 | A1* | 2/2017 | Scheib | A61B 17/07207 |

* cited by examiner

CIRCULAR STAPLER AND STAPLE HEAD ASSEMBLY THEREOF

TECHNICAL FIELD

The present disclosure relates to a circular stapler and a staple head assembly thereof, which belongs to the field of medical appliances.

BACKGROUND

A circular stapler is a kind of medical appliance often used in surgical operation of physiological tissues such as digestive tracts. These kinds of staplers often use a type of axial inner stapling. In anastomosis, two tissues move towards each other and form a circular anastomotic ring inside the tissues. The appliance is capable of discharging the tissue blood generated in the operation together with the contents, which facilitates healing of the tissues after surgery.

Currently, the circular stapler includes a staple body and an anvil assembly for mating with the staple body. The staple body includes an annular staple cartridge and a cutter both located at a far end thereof. The anvil assembly includes a cone-shaped anvil, an anvil cap fixed on top of the anvil assembly, an annular cutting pad set inside the anvil and an anvil shaft for connecting the staple body. The anvil assembly is connected to the staple body through the anvil shaft, and is capable of conducting reciprocating movement. In anastomosis, firstly, the anvil of the anvil assembly and the staple cartridge of the staple body can tightly clamp two tissues, and then the two tissues can be anastomosed by the staples sent from the staple cartridge and associated with the anvil. At the same time, the cutter is pushed out to cut off the excessive tissues.

Generally, the physiological tissues such as digestive tracts anastomosed by the circular stapler, the tissues are firstly cut by the surgical cutter. The surgical cutter will leave staples on the severed tissues. When using the circular stapler to anastomose the tissues, such staples would likely cause that the anastomotic cross does not be successfully cut off, but also it will drag the tissues. As a result, at the new anastomotic position, the tissues are torn off or the new staples can not be normally formed.

SUMMARY

In an embodiment, the present disclosure provides a circular stapler and a staple head assembly of the circular stapler.

In an embodiment, the present disclosure discloses a circular stapler including:

a staple body comprising an annular staple cartridge and an annular cutter located at a distal end of the circular stapler, the annular staple cartridge comprising a plurality of staple holes at an end face thereof;

an anvil assembly comprising an annular anvil for mating with the annular staple cartridge, an annular cutting pad for mating with the annular cutter and an anvil shaft for being moveably connected to the staple body, the annular cutting pad being arranged between the anvil shaft and the annular anvil;

wherein when the staple body and the anvil assembly are closed, the annular staple cartridge is associated with the annular anvil and the annular cutting pad to form at least two connected fixing spaces having height difference.

In an embodiment, the present disclosure discloses a staple head assembly including:

an annular staple cartridge comprising a plurality of staple holes at an end face thereof; an anvil assembly comprising an annular anvil, an annular cutting pad and an anvil shaft, the annular cutting pad being arranged between the anvil shaft and the annular anvil;

wherein the annular staple cartridge is associated with the annular anvil and the annular cutting pad to form at least two connected fixing spaces having height difference in order to tightly clamp two tissues.

In comparison with prior art, one or more embodiments may facilitate better fixing the cut staples for easily cutting. An embodiment facilitates forming a buffer between the tissues near the new formed staples and the tissues near the severed staples in order to avoid lateral slipping, thereby reducing dragging the tissues on the end face of the anvil.

ILLUSTRATED EMBODIMENTS

Detailed description of the present application will be depicted in combination with embodiments shown in figures. It should be noted that the present application should not be restricted to the embodiments, and modifications of structure, method and function to those of ordinary skill in the art according to the embodiments are all included within the protection scope of the present application.

The words used to express locations or directions in describing embodiments adopt the appliance operator as reference. An end near the operator is a proximal end and an end away from the operator is a distal end.

Figure 1:
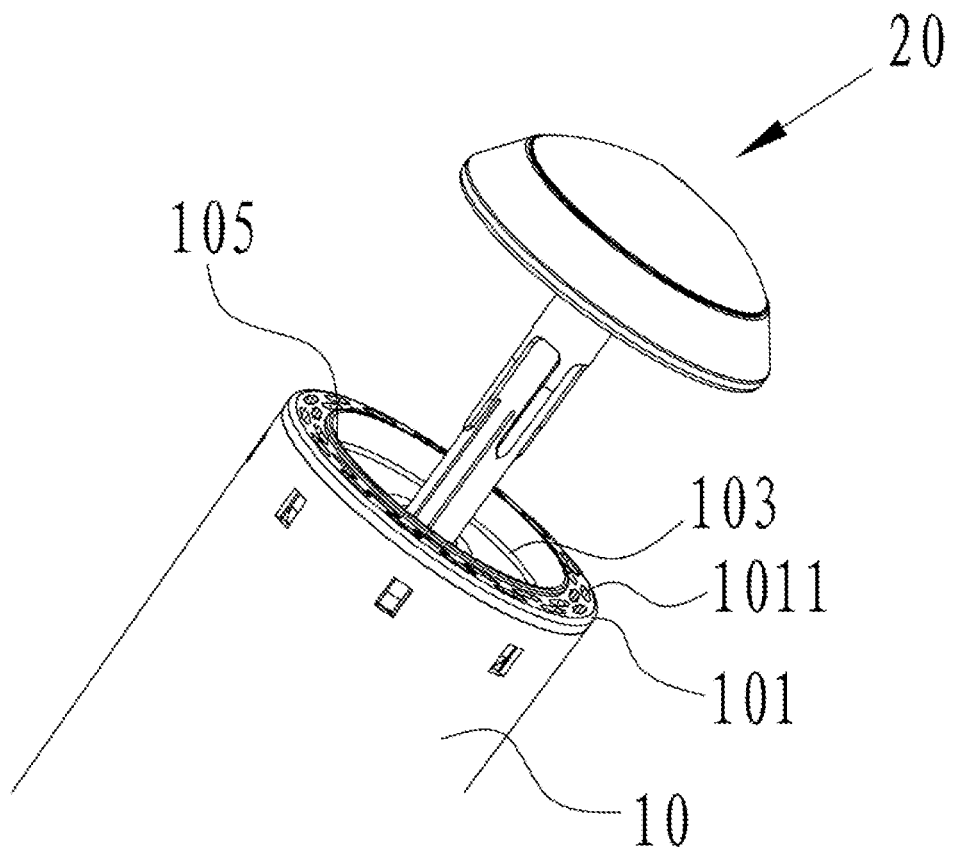
FIG. 1 is a perspective view of a part of the circular stapler in accordance with a first illustrated embodiment of the present application.
Figure 2:
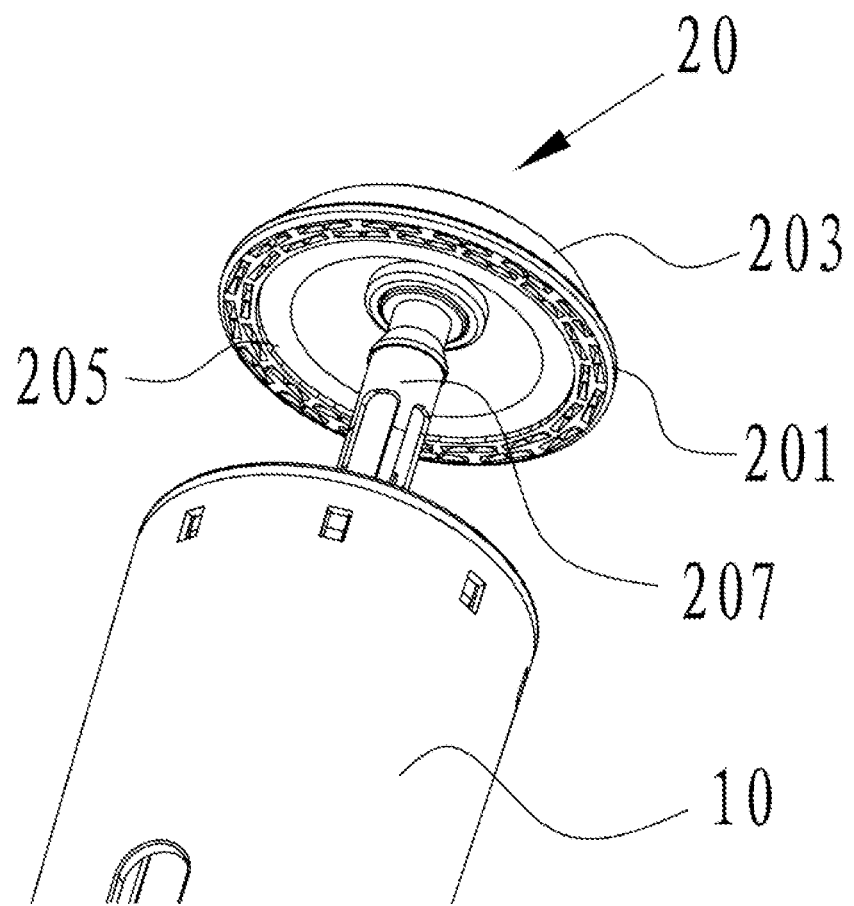
FIG. 2 is another perspective view of FIG. 1.

Referring to FIGS. 1 and 2, in accordance with a first embodiment of the present application, a circular stapler includes a staple body 10 and an anvil assembly 20 for mating with the staple body 10. The staple body 10 includes an annular staple cartridge 101 and an annular cutter 103 located at the distal end thereof. The annular staple cartridge 101 includes a plurality of staple holes 1011 at an end face thereof.

The anvil assembly 20 includes an annular anvil 201, an anvil cap 203 fixed on top of the annular anvil 201, an annular cutting pad 205 set inside the annular anvil 201 and an anvil shaft 207 for moveably connecting to the staple body 10. The annular cutting pad 205 is arranged between the anvil shaft 207 and the annular anvil 201. In anastomosis, firstly, the annular anvil 201 of the anvil assembly 20 and the annular staple cartridge 101 of the staple body 10 tightly clamp two tissues. Then, excessive tissues after stapling are cut off by the annular cutter 103. At the same time, the annular staple cartridge 101 sents out staples, associated with the annular anvil 201, to anastomotic the two tissues.

It is noted that, in the first embodiment of the present application, the anvil assembly 20 includes at least one stable ring 105 protruding beyond an end surface between the staple holes 1011 of the annular staple cartridge 101 and the annular cutter 103. The stable ring 105 will be described in detail in combination with FIGS. 3 and 4.

Figure 3:
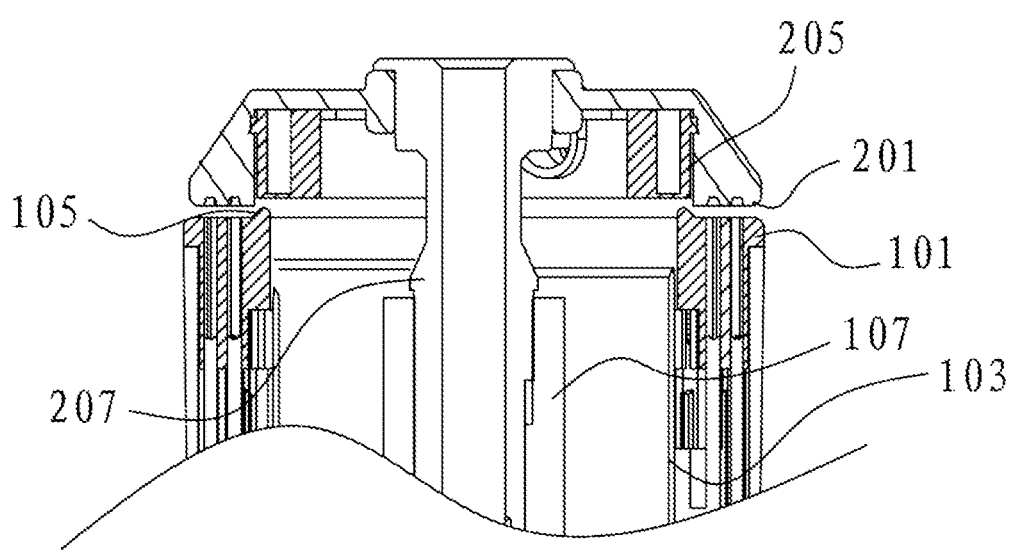
FIG. 3 is a cross-sectional view the part of the circular stapler in accordance with the first illustrated embodiment of the present application.
Figure 4:
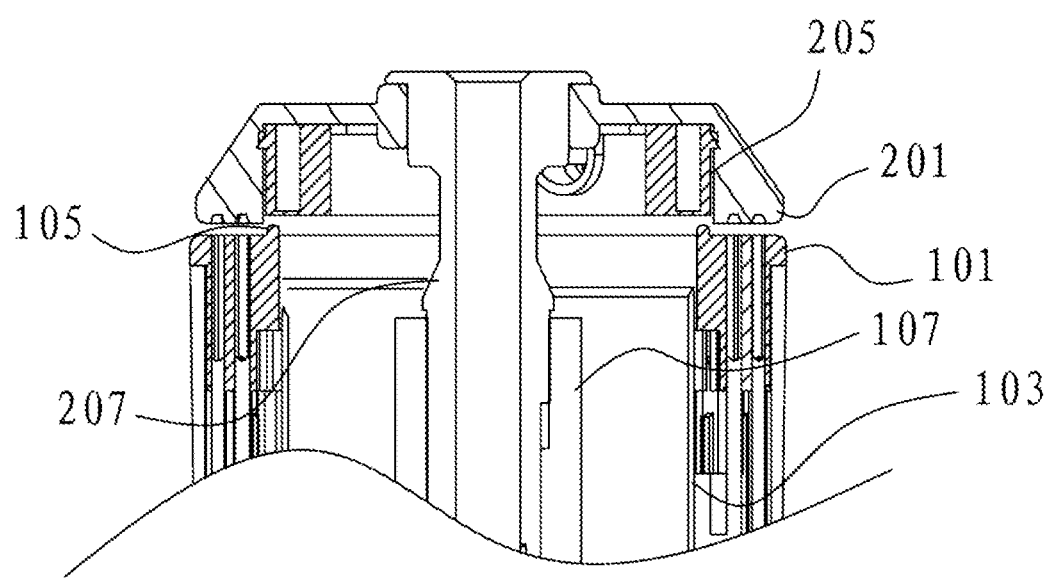
FIG. 4 is another cross-sectional view of the part of the circular stapler in accordance with the first illustrated embodiment of the present application.

Referring to FIGS. 3 and 4, in the first embodiment of the present application, the stable ring 105 is arranged at an inner surface of the annular staple cartridge 101 and extends beyond the annular staple cartridge 101. A distance between an end face of the annular cutting pad 205 and the end face of the annular staple cartridge 101 is greater than a distance between an end face of the annular anvil 201 and the end face of the annular staple cartridge 101. In other words, the annular cutting pad 205 is higher than the annular anvil 201 relative to a horizontal plane. In an embodiment, a distance between the end face of the annular cutting pad 205 and an end face of the stable ring 105 is less than or equal to the distance between the end face of the annular anvil 201 and the end face of the annular staple cartridge 101. Under this condition, when clamping the tissues, the clamp force of the annular cutting pad 205 and the stable ring 105 is greater than or equal to that of the annular anvil 201 and the annular staple cartridge 101. As a result, lateral slipping of the severed staples and tissues during cutting and stapling may be avoided or reduced, thereby reducing dragging the tissues on the end surface of the anvil 201. In an embodiment, a center point of the stable ring 105 is coaxial with a center point of the annular staple cartridge 101.

The staple body 10 also includes a hollow shaft 107. An axis of the hollow shaft 107 is coaxial with the center point of the stable ring 105 and the center point of the annular staple cartridge 101. The anvil shaft 207 is movably connected to the hollow shaft 107 and is capable of conducting reciprocating movement with respect to the hollow shaft 107. In an embodiment, the annular cutter 103 is arranged between the hollow shaft 107 and the annular staple cartridge 101, and the annular cutter 103 clings to an inner wall of the annular staple cartridge 101. In an embodiment, a distance between a sharp point of the annular cutter 103 and a horizontal plane is lower than a distance between the annular staple cartridge 101 and the horizontal plane.

In an embodiment, as shown in FIG. 3, an angle between the end face and the inner wall of the annular anvil 201 is smaller than an angle between the stable ring 105 and the end face of the annular staple cartridge 101.

In an embodiment, as shown in FIG. 4, the angle between the end face and the inner wall of the annular anvil 201 is almost the same as the angle between the stable ring 105 and the end face of the annular staple cartridge 101.

Figure 5:
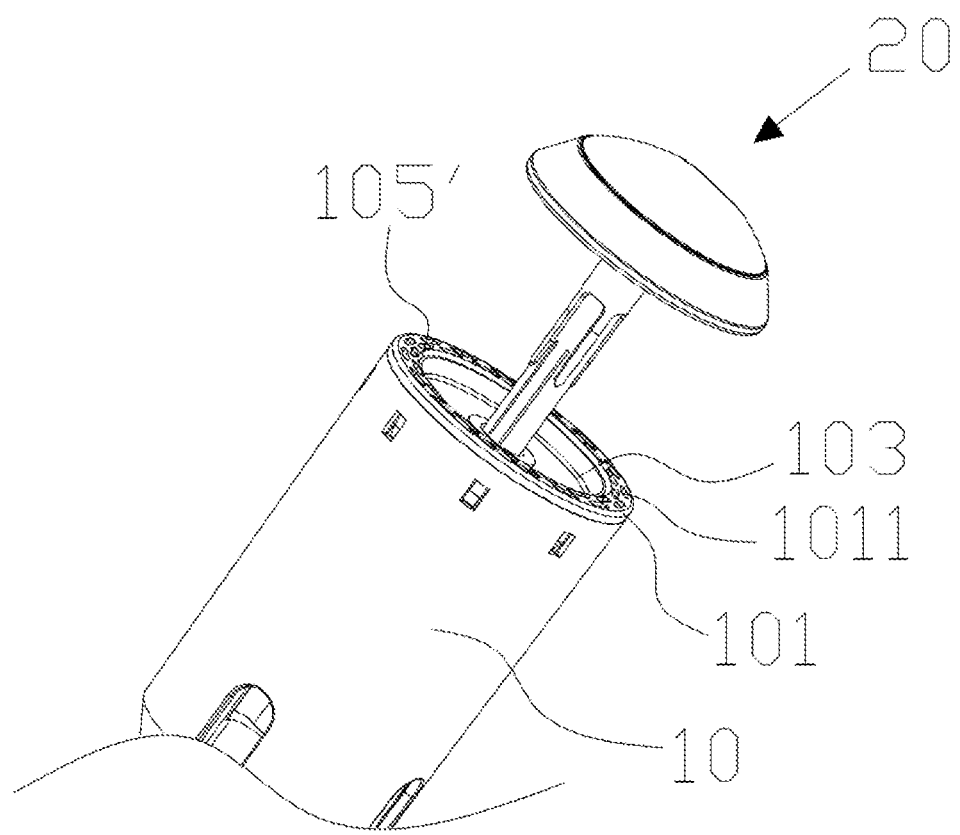
FIG. 5 is a perspective view of a part of the circular stapler in accordance with a second illustrated embodiment of the present application.
Figure 6:
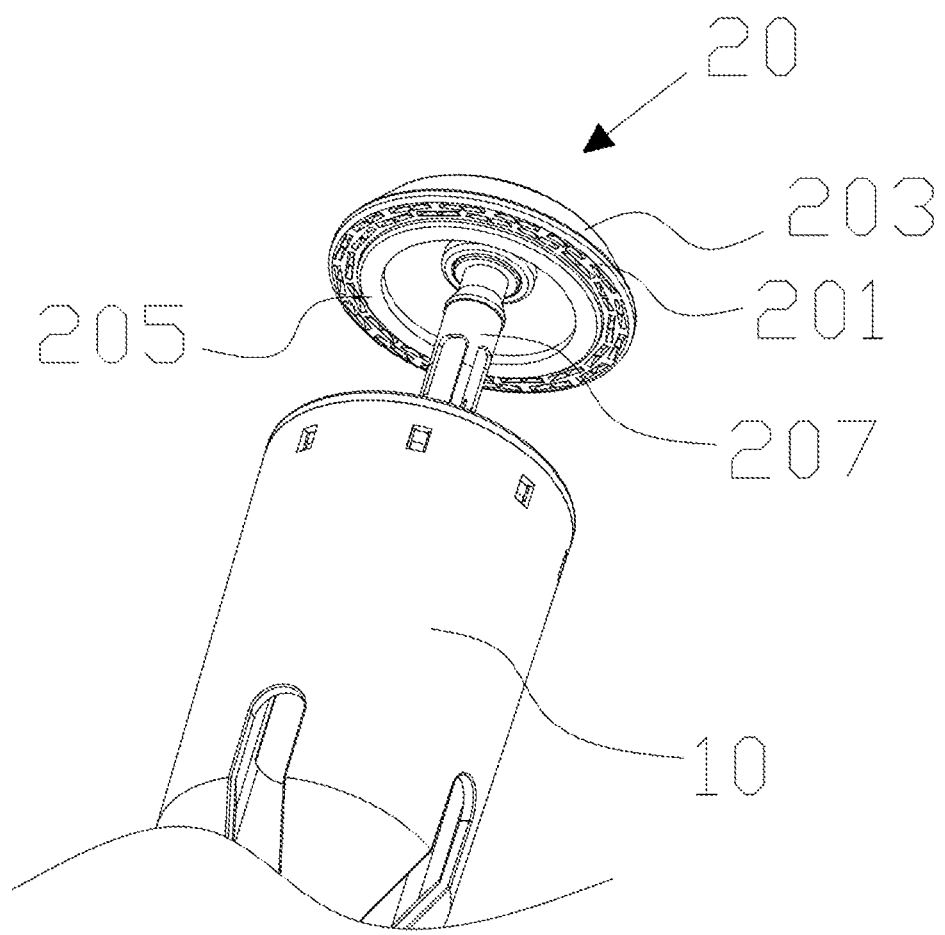
FIG. 6 is another perspective view of FIG. 5.

Referring to FIGS. 5 and 6, in accordance with a second embodiment of the present application, a circular stapler includes a staple body 10 and an anvil assembly 20 for mating with the staple body 10. The staple body 10 includes an annular staple cartridge 101 and an annular cutter 103 located at the distal end. The annular staple cartridge 101 includes a plurality of staple holes 1011 at its end surface.

The anvil assembly 20 includes an annular anvil 201, an anvil cap 203 fixed on top of the annular anvil 201, an annular cutting pad 205 set inside the annular anvil 201 and an anvil shaft 207 for moveably connecting to the staple body 10. The annular cutting pad 205 is arranged between the anvil shaft 207 and the annular anvil 201. In anastomosis, firstly, the annular anvil 201 of the anvil assembly 20 and the annular staple cartridge 101 of the staple body 10 tightly clamp two tissues. Then, excessive tissues after stapling are cut off by the annular cutter 103. At the same time, the annular staple cartridge 101 sents out staples, associated with the annular anvil 201, to anastomose the two tissues.

It is noted that, in the second embodiment of the present application, the annular staple cartridge 101 includes a concave portion 105' between the staple holes 1011 of the annular staple cartridge 101 and the annular cutter 103. The end face of the annular staple cartridge 101 is higher than a bottom face of the concave portion 105'. The annular cutting pad 205 extends beyond the annular anvil 201 along a direction towards the proximal end. The concave portion 105' will be described in detail in combination with FIGS. 7 and 8.

Figure 7:
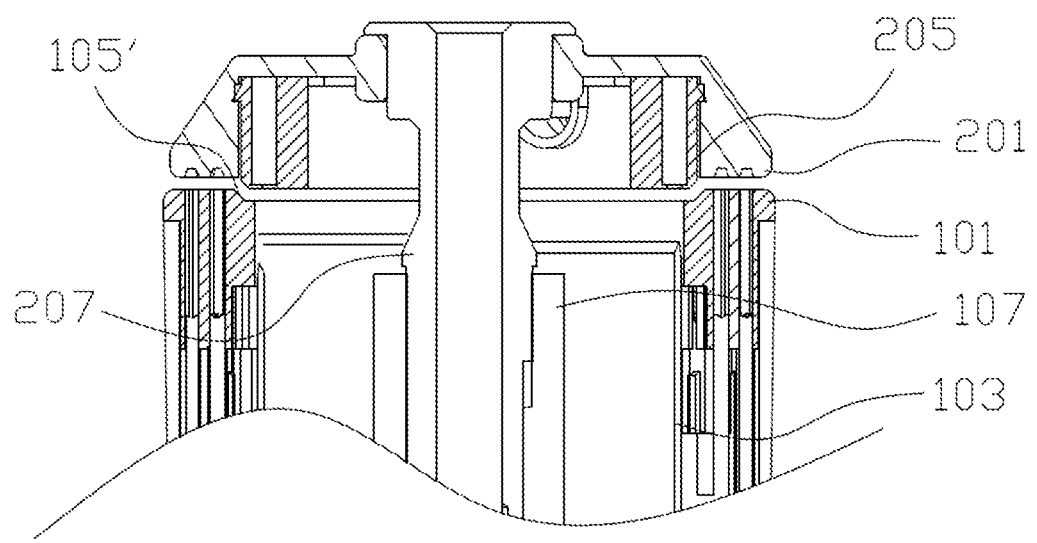
FIG. 7 is a cross-sectional view of part of the circular stapler in accordance with the second illustrated embodiment of the present application.
Figure 8:
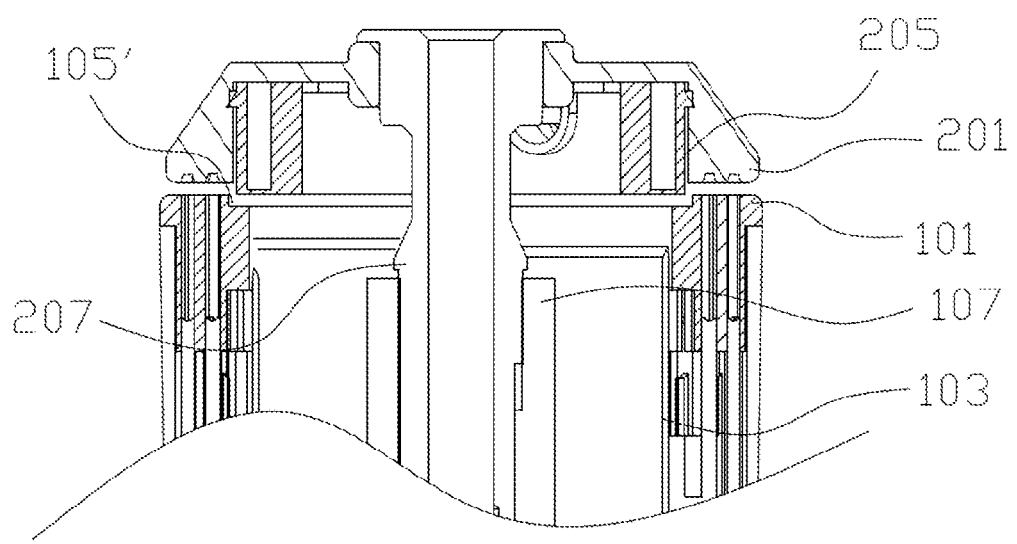
FIG. 8 is another cross-sectional view of the part of the circular stapler in accordance with the second illustrated embodiment of the present application.

Referring to FIGS. 7 and 8, in the second embodiment of the present application, the concave portion 105' is arranged at an inner surface of the annular staple cartridge 101. A distance between an end face of the annular cutting pad 205 and the end face of the annular staple cartridge 101 is less than a distance between an end face of the annular anvil 201 and the end face of the annular staple cartridge 101. In other words, the annular anvil 201 is higher than the annular cutting pad 205 relative to a horizontal plane. In an embodiment, a distance between the end face of the annular cutting pad 205 and the bottom face of the concave portion 105' is less than or equal to the distance between the end face of the annular anvil 201 and the end face of the annular staple cartridge 101. Under this condition, when clamping the tissues, the clamp force of the annular cutting pad 205 and the concave portion 105' is greater than or equal to that of the annular anvil 201 and the annular staple cartridge 101. As a result, lateral slipping of the severed staples and tissues during cutting and stapling may be avoided or reduced, thereby reducing dragging the tissues on the end surface of the anvil 201. In an embodiment, a center point of the concave portion 105' is coaxial with a center point of the annular staple cartridge 101.

The staple body 10 also includes a hollow shaft 107. An axis of the hollow shaft 107 is coaxial with the center point of the concave portion 105' and the center point of the annular staple cartridge 101. The anvil shaft 207 is movably connected to the hollow shaft 107 and is capable of conducting reciprocating movement with respect to the hollow shaft 107. In an embodiment, the annular cutter 103 is arranged between the hollow shaft 107 and the annular staple cartridge 101, and the annular cutter 103 clings to an inner wall of the annular staple cartridge 101. In an embodiment, a distance between a sharp point of the annular cutter 103 and a horizontal plane is lower than a distance between the annular staple cartridge 101 and the horizontal plane.

In an embodiment, as shown in FIG. 7, the concave portion 105' includes a bottom face and a peripheral face connected to the annular staple cartridge 101. An angle between the peripheral face and the bottom face is an acute angle or an obtuse angle. A prominent part of the annular cutting pad 205 extending beyond the annular anvil 201 has an inclined face. An angle between the inclined face and the end face of the annular cutting pad 205 is an acute angle or an obtuse angle.

In an embodiment, as shown in FIG. 8, the concave portion 105' includes the bottom face and a peripheral face connected to the annular staple cartridge 101. An angle between the peripheral face and the bottom face is a right angle. A prominent part of the annular cutting pad 205 extending beyond the annular anvil 201 has an inclined face. An angle between the inclined face and the end face of the annular cutting pad 205 is a right angle as well.

In this way, when the staple body 10 and the anvil assembly 20 are closed, the annular staple cartridge 101 associated with the annular anvil 201 and the annular cutting pad 205 forms a connected slit having at least two bending sections. Tissues in the slit will be fixed in a staggered manner. Two fixing spaces will be generated to fix the tissues and the staples respectively, in order to restrict tissue slipping. A larger space can be formed between the two fixing spaces so that the tissues can fill in the space when closing, which can avoid the tissues being squeezed too much and limit its slipping as well.

As to the defects of the existing technologies, it is impossible to completely cut off the staples either by changing materials or reducing the annular cutting pad to a minimum thickness. Even if the staples can be cut off, it happens after the annular cutting pad has been cut off, which means that tissue dragging has already been done. An embodiment of circular staplers of the present disclosure includes a stable ring 105 or a concave portion 105' which can be used to better fix the severed staples for easily cutting. An embodiment facilitates forming a buffer between the tissues near the new formed staples and the tissues near the severed staples in order to avoid lateral slipping, thereby reducing dragging the tissues on the end face of the anvil.

For those skilled in the art, apparently, the present disclosure should not be limited to the detailed of these exemplary embodiments, and embodiment of the present disclosure can be realized by other concrete forms. Therefore, no matter from which point of view, the embodiments of the present disclosure should be regarded as exemplication rather than restriction.

In addition, it is to be understood, however, that even though exemplary embodiments have been set out in the foregoing description, it does not mean that each embodiment has only one independent technical solution. The narration of the specification is only for clear description. Those of ordinary skill in the art should consider the specification as a whole. Technical solutions of all the embodiments can be appropriately combined to form other embodiments which are understandable by those skilled in the art.

What is claimed is:

1. A circular stapler, comprising:
a staple body comprising an annular staple cartridge, an annular cutter located at a distal end of the circular stapler, the annular staple cartridge comprising a plurality of staple holes at an end face thereof, and a ring arranged at an end face of the annular staple cartridge adjacent to the annular cutter; and
an anvil assembly comprising an annular anvil for mating with the annular staple cartridge, an annular cutting pad set inside the annular anvil for mating with the annular cutter and an anvil shaft moveably connected to the staple body, the annular cutting pad being arranged between the anvil shaft and the annular anvil;
wherein when the staple body and the anvil assembly are closed, a first gap exists between an end face of the annular anvil and the end face of the annular staple cartridge, and a second gap exists between an end face of the annular cutting pad and an end face of the ring, wherein a height of the second gap parallel to an axis of the anvil shaft is different from a height of the first gap parallel to the axis of the anvil shaft.

2. The circular stapler as claimed in claim 1 wherein the ring protrudes beyond an end surface between the staple holes of the annular staple cartridge and the annular cutter.

3. The circular stapler as claimed in claim 2 wherein a size of a third gap between an end face of the annular cutting pad and the end face of the annular staple cartridge is greater than the size of the first gap.

4. The circular stapler as claimed in claim 2 wherein the size of the second gap is less than the size of the first gap.

5. The circular stapler as claimed in claim 2 wherein an angle between the end face and an inner wall of the annular anvil is smaller than an angle between the ring and the end face of the annular staple cartridge.

6. The circular stapler as claimed in claim 1 wherein the ring includes a concave portion between the staple holes of the annular staple cartridge and the annular cutter, the annular cutting pad extending beyond the annular anvil along a direction towards a proximal end of the circular stapler.

7. The circular stapler as claimed in claim 6 wherein the size of a third gap between an end face of the annular cutting pad and the end face of the annular staple cartridge is less than the size of the first gap.

8. The circular stapler as claimed in claim 6 wherein the size of the second gap is less than the size of the first gap.

9. The circular stapler as claimed in claim 6 wherein the concave portion comprises a bottom face and a peripheral face connected to the annular staple cartridge, an angle between the peripheral face and the bottom face being a right angle or an obtuse angle.

10. A staple head assembly, comprising:
an annular staple cartridge comprising a plurality of staple holes at an end face thereof;
an anvil assembly comprising an annular anvil, an annular cutting pad and an anvil shaft, the annular cutting pad being arranged inside the annular anvil between the anvil shaft and the annular anvil; and
a ring arranged at an end face of the annular staple cartridge adjacent to the annular cutter,
wherein, in operation, a first gap exists between an end face of the annular anvil and the end face of the annular staple cartridge, and a second gap exists between an end face of the annular cutting pad and the end face of the ring, wherein a height of the second gap parallel to an axis of the anvil shaft is different from a height of the first gap parallel to the axis of the anvil shaft.

11. The staple head assembly as claimed in claim 10 wherein the ring protrudes beyond an inner annual surface of the annular staple cartridge.

12. The staple head assembly as claimed in claim 11 wherein a size of a third gap between an end face of the annular cutting pad and the end face of the annular staple cartridge is greater than the size of the first gap.

13. The staple head assembly as claimed in claim 11 wherein the size of the second gap is less than the size of the first gap.

14. The staple head assembly as claimed in claim 11 wherein an angle between the end face and an inner wall of the annular anvil is smaller than an angle between the ring and the end face of the annular staple cartridge.

15. The staple head assembly as claimed in claim 10 wherein the ring includes a concave portion at the inner annual surface of the annular staple cartridge, the annular cutting pad extending beyond the annular anvil.

16. The staple head assembly as claimed in claim 15 wherein a size of a third gap between an end face of the annular cutting pad and the end face of the annular staple cartridge is less than the size of the first gap.

17. The staple head assembly as claimed in claim 15 wherein the size of the second gap is less than the size of the first gap.

18. The staple head assembly as claimed in claim 15 wherein the concave portion comprises a bottom face and a peripheral face connected to the annular staple cartridge, an angle between the peripheral face and the bottom face being a right angle or an obtuse angle.

* * * * *